United States Patent [19]
Correia et al.

[11] Patent Number: 5,401,876
[45] Date of Patent: Mar. 28, 1995

[54] SYNTHESIS OF CHLOROACETIC ACIDS

[75] Inventors: Yves Correia, Chateau Arnoux; Daniel Pellegrin, Grenoble, both of France

[73] Assignee: Elf Atochem S.A., Puteaux, France

[21] Appl. No.: 95,224

[22] Filed: Jul. 23, 1993

[30] Foreign Application Priority Data

Jul. 23, 1992 [FR] France .................................. 92 09095

[51] Int. Cl.$^6$ ............................................. C07B 39/00
[52] U.S. Cl. ................................................. 562/603
[58] Field of Search ........................................ 562/603

[56] References Cited

U.S. PATENT DOCUMENTS

| | | | |
|---|---|---|---|
| 2,826,610 | 3/1958 | Morris et al. | 562/603 |
| 4,003,723 | 1/1977 | Schäfer et al. | 562/603 |
| 4,383,121 | 3/1983 | Sugamiga et al. | 562/603 |

FOREIGN PATENT DOCUMENTS

| | | | |
|---|---|---|---|
| 552754 | 2/1958 | Canada | 562/603 |
| 749128 | 10/1970 | France | 562/603 |
| 0127329 | 10/1981 | Japan | 562/603 |
| 109769 | 10/1964 | Netherlands | 562/603 |
| 6031 | of 1910 | United Kingdom | 562/603 |
| 1404503 | 6/1988 | U.S.S.R. | 562/603 |

OTHER PUBLICATIONS

CA 78(20):128110p Opp et al "Removal of Chlorine, Phosgene, and Hydrogen Chloride from waste Gasses", DE2121403, 1972, Abs. only.

*Primary Examiner*—Raymond J. Henley, III
*Assistant Examiner*—Keith MacMillan
*Attorney, Agent, or Firm*—Burns, Doane, Swecker & Mathis

[57] ABSTRACT

Chloroacetic acids and essentially pure hydrochloric acid are prepared by chlorinating acetic acid in the presence of a catalytically effective amount of acetic anhydride, acetyl chloride, or admixture thereof, whereby byproducing a gaseous stream of crude hydrochloric acid, contacting such gaseous stream with active charcoal to remove the chlorine values therefrom, separating (i) pure hydrochloric acid and (ii) remaining products from the gaseous stream thus purified, and recycling such remaining products (ii) to the medium of chlorination.

16 Claims, 1 Drawing Sheet

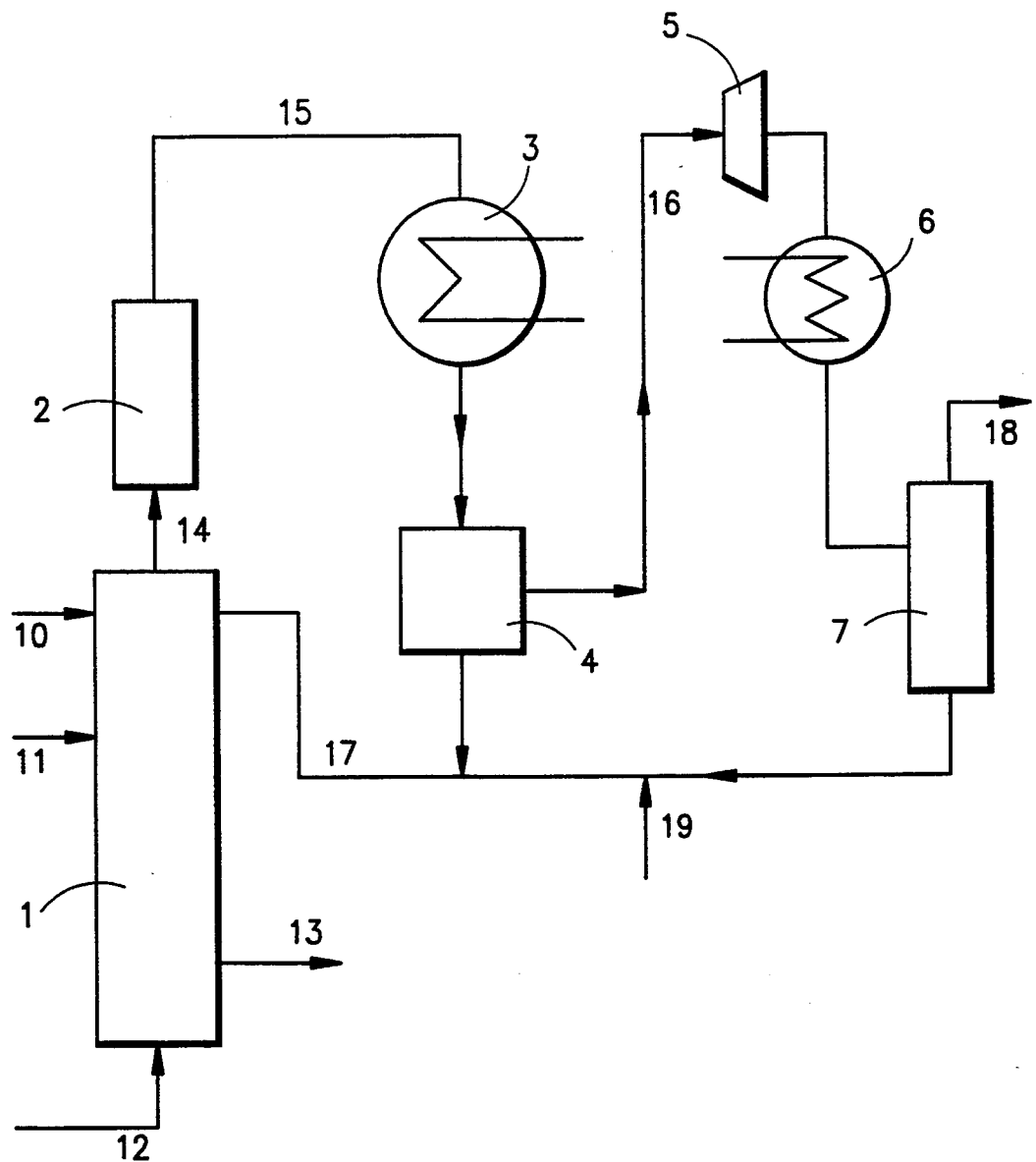

SYNTHESIS OF CHLOROACETIC ACIDS

BACKGROUND OF THE INVENTION

1. Field of the Invention

The present invention relates to an improved process for the preparation of chloroacetic acids, and, more especially, to an improved process for the chlorination of acetic acid wherein the byproduct crude gaseous hydrochloric acid, containing chlorine and acetyl chloride values, is purified and pure HCl recovered, while other products are recycled to the medium of chlorination.

2. Description of the Prior Art

Hydrochloric acid is produced, for example as a byproduct during the synthesis of chloroacetic acids, by reacting chlorine with acetic acid in the presence of acetic anhydride or of acetyl chloride. Such synthesis is described in Ullman's *Encyclopaedia of Industrial Chemistry*, 5th Edition, Vol. A6, pages 537–541.

Acetic anhydride, acetyl chloride, or mixture thereof, can be employed as a catalyst in this reaction. The reaction mechanisms are as follows:

$$(CH_3CO)_2O + Cl_2 \longrightarrow$$

$$ClCH_2\overset{O}{\overset{\|}{C}}-O-\overset{O}{\overset{\|}{C}}CH_3 + HCl$$

$$ClCH_2\overset{O}{\overset{\|}{C}}-O-\overset{O}{\overset{\|}{C}}-CH_3 + CH_3COOH \longrightarrow$$

$$ClCH_2COOH + (CH_3CO)_2O$$

$$CH_3COCl + Cl_2 \rightarrow ClCH_2COCl + HCl$$

$$ClCH_2COCl + CH_3COOH \rightarrow ClCH_2COOH + CH_3COCl$$

A fraction of the acetic anhydride is also converted to acetyl chloride:

$$(CH_3CO)_2O + HCl \rightarrow CH_3COCl + CH_3COOH$$

Thus produced are (i) a liquid phase containing acetic acid, monochloroacetic acid, acetyl chloride, chloroacetyl chloride, optionally acetic anhydride and the chloride thereof, and a minor amount of dichloroacetic acid and (ii) a gas phase essentially comprising hydrochloric acid and a few percent of chlorine, acetyl chloride, chloroacetyl chloride, acetic acid and monochloroacetic acid. This hydrochloric acid must be purified before being used, for example, as a reagent in an oxychlorination reaction. It is also preferable to recover the above-indicated compounds contained in the gaseous hydrochloric acid stream to permit recycling same to the synthesis of chloroacetic acids.

Techniques for the purification of such crude gaseous hydrochloric acid stream are known to this art.

FR-2,311,749 and JP-63/50,303 (Kokai) relate that purification by condensation requires low temperatures taking account of the boiling point of acetyl chloride. It is necessary to employ both pressure and a low temperature, but the impure gaseous hydrochloric acid thus provided is very corrosive to compressors.

FR-2,311,749 describes washing such crude gaseous hydrochloric acid stream with a concentrated solution of sulfuric acid and of acetic acid and then drying the washed product with concentrated sulfuric acid.

Said JP-63/50,303 (Kokai), published Mar. 3, 1988, describes washing the crude gaseous hydrochloric acid stream, containing acetyl chloride below a specified amount, with sulfuric acid. The acetyl chloride contained in the crude hydrochloric acid stream is converted into acetyl sulfate.

Nonetheless, such processes require sulfuric acid and complicated mechanical apparatus.

SUMMARY OF THE INVENTION

Accordingly, a major object of the present invention is the provision of an improved, far simpler total synthesis of chloroacetic acids which does not require the addition of an extraneous compound such as sulfuric acid.

Indeed, it has now unexpectedly been determined that it suffices to remove the chlorine contained in such crude hydrochloric acid, thus permitting same to be compressed without risk of corrosion. To this end, it is sufficient to contact the crude gaseous hydrochloric acid stream with active charcoal.

It has also now been determined that chlorine reacts with acetyl chloride in the vapor phase on active charcoal, and in a very short period of time, to form chloroacetyl chloride.

Briefly, the present invention features an improved process for the synthesis of chloroacetic acids by chlorination of acetic acid in the presence of acetic anhydride or of acetyl chloride, thereby producing a gaseous stream of crude hydrochloric acid as a byproduct, and which comprises:

(a) contacting such gas stream with active charcoal until the chlorine values contained therein have been removed, (b) separating, in the stream obtained in step (a), by means of at least one compression (pressurization) and one cooling sequence, (i) pure hydrochloric acid and (ii) other products, (c) recycling said other products (ii) into the reactor or reaction zone for the synthesis of the chloroacetic acids.

BRIEF DESCRIPTION OF THE DRAWING

The FIGURE of Drawing is a schematic/diagrammatic illustration of suitable apparatus for carrying out the process of the present invention.

DETAILED DESCRIPTION OF PREFERRED EMBODIMENTS OF THE INVENTION

More particularly according to the present invention, the synthesis of chloroacetic acids can be carried out by chlorination of acetic acid in the presence of acetic anhydride or of acetyl chloride as catalyst therefor. Whether acetic anhydride or acetyl chloride is used, acetyl chloride is always formed. Whether the synthesis is in the gas or liquid phase, the hydrochloric acid byproduct is always obtained in the gaseous form. This acid contains a few percent of chlorine ($Cl_2$), of acetyl chloride, of chloroacetyl chloride, of acetic acid and of monochloroacetic acid.

Although it is possible to use any type of active charcoal and in any form, it is advantageous that it be constituted as a fixed bed and in the form of granules in order to minimize the pressure drop of the gas stream to be purified. The charcoal is preferably employed in the form of granules of a size ranging from 2 to 3 mm. The specific surface of the charcoal advantageously ranges from 300 to 1,200 m²/g.

To attain a significant reaction rate, the reaction is carried out at a temperature ranging from 50° to 200° C. and preferably from 100° to 150° C.

Depending on the amount of chlorine and the temperature, a residence time of the gaseous hydrochloric acid to be purified advantageously ranges from 0.1 to 20 seconds.

The pressure is not critical; the hydrochloric acid to be purified is characteristically present at a pressure of from 0.5 to 5 bars absolute and at a temperature of from 50° to 100° C. To obtain complete disappearance or stripping of the chlorine, it is apparent that the molar amount of acetyl chloride must be greater than that of the chlorine. It was observed that if the acetyl chloride to chlorine molar ratio is greater than 5, it is possible to completely remove the chlorine, if its content ranges from 0.2% to 0.8% in the stream to be purified, for a residence time of 2 to 3 seconds and at a temperature of 120° to 150° C.

Step (b) is per se known to this art. The stream obtained at the end of step (a) is cooled at a temperature of from −25° C. to −35°0 C. Thus obtained are a liquid phase consisting essentially of chloroacetyl chloride, of acetic acid, of monochloroacetic acid and of a minor amount of acetyl chloride, and a gas phase of hydrochloric acid and of acetyl chloride.

This gas phase is advantageously compressed at 10 bars and then cooled to at least −33° C. to liquefy the hydrochloric acid (HCl). Such hydrochloric acid is distilled and pure hydrochloric acid is obtained at the head and acetyl chloride containing dissolved HCl is obtained at the base of the column.

The fraction obtained at the base of the column and the liquid phase obtained in the condenser before compression are recycled into the reactor for the synthesis of chloroacetic acids.

It is also within the scope of the invention to conduct a number of coolings, a number of compressions, coolings between each compression, and the like.

In step (c), the products which were contained in the gaseous hydrochloric acid stream to be purified prior to step (a), except for the chlorine which was converted into chloroacetyl chloride, are recycled to the synthesis reaction zone. The chlorine is thus recovered.

The FIGURE of Drawing illustrates one embodiment of the process of the invention for the synthesis of monochloroacetic acid, catalyzed by means of acetyl chloride. Acetic acid is introduced via inlet 10 and chlorine via inlet 12 into a reactor 1. The reaction mixture is drawn off via line 13 in order to separate the monochloroacetic acid therefrom, and the acetyl chloride, acetic acid and chloroacetyl chloride are recycled via conduit 11. The gaseous hydrochloric acid stream exits via line 14 and is transferred through the active charcoal bed 2. Via line 15 the stream, purified or stripped of its chlorine values, is condensed at −30° C. in an exchanger 3 and conveyed to a separator 4. The gaseous hydrochloric acid, still containing acetyl chloride, is removed via line 16, and a liquid consisting essentially of chloroacetyl chloride, of acetic acid, of monochloroacetic acid and of a minor amount of acetyl chloride, is recycled via line 17 into the reactor 1.

The stream 16 is compressed at 10 bars in a compressor 5, cooled to −33° C. in the exchanger 6 and then distilled in column 7. A stream 18 of essentially pure hydrochloric acid is recovered at the head of the column and the column bottoms, including acetyl chloride and hydrochloric acid, are mixed with the stream 17 to be recycled to the reactor 1. The stream 19 is acetic anhydride, introduced to compensate for process losses.

In order to further illustrate the present invention and the advantages thereof, the following specific example is given, it being understood that same is intended only as illustrative and in nowise limitative.

EXAMPLE

The reaction was carried out in the apparatus shown in the FIGURE of Drawing.

A reactor for the chlorination of acetic acid operated continuously and homogeneously. The pressure was 5 bars absolute and the temperature 130° C.

The gas emerging from the reactor 1 had the composition by volume given below (stream 14):

| Acetic acid | 2.3% |
| Monochloroacetic acid | 1.4% |
| Acetyl chloride | 4.1% |
| Monochloroacetyl chloride | 1.3% |
| HCl | 90.4% |
| $Cl_2$ | 0.5% |

It was transferred through an 800 m²/g active charcoal bed maintained at 130° C., at a residence time of 2 seconds.

The hydrochloric acid obtained via outlet 18 contained only 25 ppm of chlorine.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of chloroacetic acids, comprising chlorinating acetic acid in the presence of a catalytically effective amount of acetic anhydride, acetyl chloride, or admixture thereof, whereby a gaseous byproduct stream including hydrochloric acid and chlorine is produced, wherein the process further comprises (a) contacting said gaseous byproduct stream with active charcoal to remove chlorine values therefrom, (b) separating (i) pure hydrochloric acid and (ii) remaining products from the gaseous stream, and then (c) recycling said remaining products (ii) to the medium of chlorination.

2. The process as defined by claim 1, said gaseous stream further comprising acetyl chloride and having a molar ratio acetyl chloride/chlorine of greater than 5.

3. The process as defined by claim 2, comprising contacting said gaseous stream with the active charcoal for from 2 to 3 seconds at a temperature ranging from 120° to 150° C.

4. The process as defined by claim 1, comprising separating said (i) pure hydrochloric acid via the liquefaction thereof.

5. The process as defined by claim 4, comprising liquefaction via at least one pressurization/cooling sequence.

6. The process as defined by claim 4, comprising distilling said liquid pure hydrochloric acid to further purify same and recycling distilland to the medium of chlorination.

7. The process as defined by claim 1, said active charcoal comprising a particulate fixed bed thereof.

8. The process as defined by claim 7, said active charcoal particulates having a particle size ranging from 2 to 3 mm.

9. The process as defined by claim 8, said active charcoal particulates having a specific surface ranging from 300 to 1,200 m²/g.

10. The process as defined by claim 1, said gaseous byproduct stream further comprising acetyl chloride where the molar amount of the acetyl chloride is greater than that of chlorine.

11. In a process for the preparation of chloroacetic acid comprising the chlorination of acetic acid and in which a gaseous byproduct stream including hydrochloric acid and chlorine is produced, wherein the improvement comprises (a) contacting the gaseous byproduct stream with active charcoal to remove chlorine therefrom, (b) separating (i) hydrochloric acid and (ii) remaining products from the gaseous stream, and then (c) recycling the remaining products (ii) to the medium of chlorination.

12. The process as defined by claim 11, said active charcoal comprising a particulate fixed bed thereof.

13. The process as defined by claim 12, said active charcoal particulates having a particle size ranging from 2 to 3 mm.

14. The process as defined by claim 13, said active charcoal particulates having a fixed surface area ranging from 300 to 1200 m₂/g.

15. The process as defined by claim 11, said gaseous byproduct stream further comprising acetyl chloride and having in molar ratio of acetyl chloride/chlorine that is greater than 5.

16. The process as defined by claim 15, comprising contacting said gaseous byproduct stream with active charcoal from 2 to 3 seconds and at a temperature ranging from 120° to 150° C.

* * * * *